United States Patent [19]
Frickey et al.

[11] Patent Number: 4,806,470
[45] Date of Patent: * Feb. 21, 1989

[54] ANALYTICAL ELEMENT AND METHOD FOR THEOPHYLLINE DETERMINATION HAVING INCREASED ALKALINE PHOSPHATASE ISOENZYME

[75] Inventors: Paul H. Frickey; Gary E. Norton, both of Rochester, N.Y.

[73] Assignee: Eastman Kodak Company, Rochester, N.Y.

[*] Notice: The portion of the term of this patent subsequent to Nov. 1, 2005 has been disclaimed.

[21] Appl. No.: 900,068

[22] Filed: Aug. 25, 1986

[51] Int. Cl.$^4$ .................. C12Q 1/42; C12N 9/99
[52] U.S. Cl. ..................... 435/21; 435/184; 435/805; 422/56
[58] Field of Search ............... 435/21, 184, 805, 810; 422/56; 436/825

[56] References Cited

U.S. PATENT DOCUMENTS 4,264,727 4/1981 Kolehmainen et al. ............... 435/8

OTHER PUBLICATIONS

Vinet et al., *Clin. Chem.*, 25:8, pp. 1370–1372 (1979).
Vinet et al., *Clin. Biochem.*, 11:2, pp. 57–61 (1978).
Fawaz et al., *Z. Physiol. Chem.*, 353, pp. 1779–1783 (1972).
Ansari et al., *Clinica Chimica Acta*, 118, pp. 135–139 (1982).

*Primary Examiner*—Esther M. Kepplinger
*Attorney, Agent, or Firm*—J. Lanny Tucker

[57] ABSTRACT

Theophylline can be determined with an analytical element and method which utilize the inhibition, by theophylline, of alkaline phosphatase activity on an appropriate substrate. The assay is carried out at a pH of 9 or less. The element comprises an absorbent carrier material, a suitable buffer and first and second zones in fluid contact. The isoenzyme of alkaline phosphatase and a suitable substrate for the isoenzyme are located in different zones of the element. The isoenzyme is present in one of the zones in an amount of at least about 100 I.U./m$^2$. This level of isoenzyme reduces or eliminates bias caused by endogenous alkaline phosphatase and hemoglobin during an assay.

18 Claims, No Drawings

ANALYTICAL ELEMENT AND METHOD FOR THEOPHYLLINE DETERMINATION HAVING INCREASED ALKALINE PHOSPHATASE ISOENZYME

FIELD OF THE INVENTION

The present invention relates to clinical chemistry and to the assay of biological fluids for theophylline. More specifically, it relates to a dry analytical element and a method for the determination of theophylline in human biological fluids.

BACKGROUND OF THE INVENTION

Theophylline is a drug frequently administered for treatment of asthma and pulmonary diseases. For the drug to be used successfully without serious side-effects, it must be frequently and carefully monitored in a patient because it has a relatively narrow therapeutic range of use, that is, 1-2 mg/dl.

Numerous techniques have been used to determine the amount of theophylline in human serum. Most of these techniques have serious drawbacks. For example, known spectrophotometric methods require large sample volumes, extensive pretreatment and suffer from interferences by similarly structured xanthines, such as caffeine and theobromine. Known gas chromatograpnic methods are more specific, but require derivitization and are time consuming.

Nonisotropic immunoassay techniques are most frequently used because they provide rapid results and are simple to use. Although satisfactory sensitivity has been generally obtained with immunoassay techniques, it has been found recently that they may produce highly elevated results depending upon a patient's renal condition and the specificity of the antibody used in the assay. Moreover, immunoassays require the use of generally costly reagents which have limited stability.

High performance liquid chromatography techniques are also known. These techniques vary in specificity depending upon whether pretreatment of the test sample is carried out. Organic extraction steps are necessary to improve the accuracy and specificity of the assay. Many chromatography methods are susceptible to interferences from a number of substances including some common antibiotics. Other disadvantages include the need for expensive instrumentation and a specialized technical staff to perform the assays.

It is known that theophylline can be determined by measuring its inhibitory effect on alkaline phosphatase activity. However, when assaying human biological fluids in this manner, it is known that endogenous alkaline phosphatase can affect the assay and render inaccurate results on the high side. Endogenous alkaline phosphatase must then be destroyed or removed in some manner prior to the assay to avoid this problem.

In a literature article by B. Vinet and L. Zizian [*Clin. Chem.*, 25: 8, pp. 1370-1372 (1979)], an assay for theophylline in human serum is described in which the drug was extracted from the serum sample using chloroform/isopropanol to separate the theophylline from an unknown quantity of endogenous alkaline phosphatase prior to the actual determination of theophylline. The amount of theophylline was determined at pH 9.4 by measuring the amount of inhibition of bovine alkaline phosphatase activity which occurred due to the presence of theophylline. This assay has several serious drawbacks, however. It is limited to solution assays. Further, it is slow and tedious due to the multiple extraction steps required to separate endogenous alkaline phosphatase from theophylline prior to actual determination of the drug.

A significant advance in the art is described in commonly assigned and copending U.S. Ser. No. 692,473, filed Jan. 18, 1985 by Norton and entitled Analytical Element and Method for Determination of Theophylline by Enzyme Inhibition. The element described and claimed therein, however, contains from about 10 to about 50 I.U./m$^2$ of the alkaline phosphatase isoenzyme needed for the assay. The preferred amounts disclosed are from about 20 to about 40 I.U./m$^2$.

While the element described above provides a simple and rapid assay for theophylline, it has been found that further improvement is needed to reduce the effect of endogenous alkaline phosphatase and hemoglobin in biological test fluids on the assay. Assays carried out with this element are undesirably biased by the presence of these interferents.

SUMMARY OF THE INVENTION

The problems noted above are overcome with a dry analytical element for the determination of theophylline comprising an absorbent carrier material, a buffer which maintains the pH at 9 or less during the determination and, in fluid contact, first and second zones, the first zone containing at least about 100 I.U./m$^2$ of an isoenzyme of alkaline phosphatase which is capable of acting on a substrate for the isoenzyme at a pH of 9 or less, and the second zone containing a substrate for the isoenzyme.

A preferred embodiment of this invention is a dry analytical element comprising, in fluid contact, a porous spreading zone and at least one additional zone, the element containing at least about 100 I.U./m$^2$ of an isoenzyme of alkaline phosphatase which is capable of acting on a substrate for the isoenzyme at a pH of 9 or less, and a substrate for the isoenzyme, provided the phosphatase and substrate are in different zones of the element, the element further containing a buffer which is capable of maintaining the pH at 9 or less during the determination, provided that substantially all of the buffer is in the porous spreading zone.

Further, this invention provides a method for the determination of theophylline comprising the steps of:

A. at a pH of 9 or less, contacting a sample of a biological fluid suspected of containing theophylline with the dry analytical element described above, and B. determining a detectable change resulting from the contact.

The present invention provides a simple and rapid assay for theophylline having all of the advantages of the element and assay described and claimed in copending U.S. Ser. No. 692,473, noted above. In addition, the assay of the present invention exhibits less interference from endogenous alkaline phosphatase and hemoglobin in the biological test fluids.

Further, it was found that the present invention exhibits increased rate range and improved keeping independent of the improvements obtained with the invention described and claimed in copending and commonly assigned U.S. Ser. No. 900,069 filed on even date herewith and entitled ANALYTICAL ELEMENT AND METHOD FOR THEOPHYLLINE DETERMINATION USING BUFFER IN SPREADING ZONE.

These improvements were achieved unexpectedly by significantly increasing the amount of alkaline phosphatase isoenzyme in the element. Specifically, the isoenzyme is present in an amount of at least about 100 I.U./m$^2$ as opposed to the 10-50 I.U./m$^2$ used in the elements described in U.S. Ser. No. 692,473 noted above.

DETAILED DESCRIPTION OF THE INVENTION

The present invention relates to the determination of theophylline in biological fluids, and especially human biological fluids. As used herein, determination refers to either qualitative or quantitative measurements of the amount of theophylline in a test sample. In particular, this invention can be used to determine theophylline in human biological fluids which contain endogenous alkaline phosphatase (that is, naturally occurring enzyme) in any of its enzymatic forms (for example, liver, intestinal, placental or bone). For example, this invention can be advantageously used to assay sera, whole blood, plasma, spinal fluid, sputum, bile, saliva, and other biological fluids. It is also possible to use the invention to assay fluid preparations of tissue such as human skeletal muscle, kidney, placenta, heart, intestine, lung or other tissue. The preferred biological fluids used in the practice of this invention are human sera and whole blood.

Theophylline is determinable in the practice of this invention by inhibiting the activity of alkaline phosphatase, an enzyme which can act on a number of substrates to produce a detectable reaction product. For example, the following representative equation illustrates the production of a detectable dye by the action of alkaline phosphatase using a typical substrate, p-nitrophenyl phosphate:

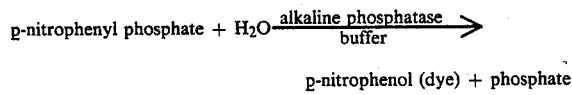

p-nitrophenyl phosphate + H$_2$O $\xrightarrow[\text{buffer}]{\text{alkaline phosphatase}}$ p-nitrophenol (dye) + phosphate The dye can then be colorimetrically detected with suitable spectrophotometric detection equipment. The amount of theophylline present in the test sample contacted with the substrate and enzyme is inversely proportional to the amount of dye measured.

The present invention is practiced at a pH of 9 or less, and preferably at a pH of from 7 to 9. As noted in U.S. Ser. No. 692,473, noted above, endogenous alkaline phosphatase in human fluids has reduced activity at a pH of 9 or less. Therefore, the presence of endogenous isoenzymes of alkaline phosphatase in a test sample has less effect on an assay for theophylline carried out at pH 9 or less. However, isoenzymes of alkaline phosphatase which are not inactivated in an environment of pH 9 or less can be used in the present invention to indicate the presence of theophylline. Any isoenzyme from any suitable source which has that desired property, that is, activity measurable at a pH of 9 or less, is useful in the practice of this invention. Particularly useful isoenzymes are those obtained from bovine sources, for example, tissues and organs (such as liver) of cattle or calves. Isoenzymes from various other sources (for example microorganisms, avian and nonhuman mammalian sources) are also useful. It is well within the skill of a worker in clinical chemistry to find isoenzymes which will be useful in the practice of this invention.

One or more of a variety of alkaline phosphatase substrates can be used in the practice of this invention.

The substrate must be such that upon enzymatic reaction with the isoenzyme, a directly detectable change occurs. For example, the substrate is converted into one or more detectable reaction products, such as a chromogen, fluorogen, radioisotopically labeled species, and other suitable detectable products. The detectable change measured during the assay can be the appearance or disappearance of such a detectable product, or the change of one detectable product into another. Alternatively, the detectable change can be brought about through a series of reactions which are initiated by the action of the isoenzyme on the substrate. For example, the alkaline phosphatase isoenzyme can act on the substrate to release another enzyme or reagent which then is used in one or more reactions to produce a detectable product. The detectable product may be directly measurable, or require some physical separation or handling for measurement.

In a preferred embodiment of this invention, the assay provides a chromogen or fluorogen as a detectable product of the enzymatic reaction. Generally, the substrates which are useful in such reactions have a phosphate group which is cleaved from the substrate molecule during the enzymatic reaction. Such substrates include organic mono- or diesters of phosphoric acid or salts thereof. Examples of particularly useful substrates include p-nitrophenyl phosphate, phenolphthalein monophosphate, phenolphthalein diphosphate, thymolphthalein monophosphate, indoxyl phosphate, phenyl phosphate, α-naphthol phosphate, ⊖-naphthol phosphate, α-glycerol phosphate, o-methylfluorescein phosphate, o-carboxyphenyl phosphate, alkali metal salts thereof and others known in the art, for example, in U.S. Pat. No. 3,425,912 (issued Feb. 4, 1969 to Deutsch et al) and European Patent Publication No. 61,731 (published Oct. 6, 1982). Preferred substrates are p-nitrophenyl phosphate and 4-(4-nitro-2-methylsulfonyl phenylazo)-naphthol-1-phosphate.

The isoenzyme and substrate must be kept separated in different zones of the element until contacted with the liquid test sample. The amount of isoenzyme in the element is critical to obtaining the advantages noted above. The element must contain at least about 100 I.U./m$^2$ of the isoenzyme. In a preferred embodiment, the isoenzyme is present in a coverage of at least about 125 I.U./m$^2$. In the context of this disclosure, I.U. represents the International Unit for isoenzyme activity defined as one I.U. being the amount of isoenzyme activity required to catalyze the conversion of 1 micromole of substrate per minute under standard pH and temperature conditions for the isoenzyme.

The amount of substrate in the element can be varied widely. Generally it is present in an amount of from about 1 to about 5, and preferably from about 2 to about 4, g/m$^2$. Other addenda (for example, surfactants, binders and buffers) are incorporated into the element in amounts which are within the skill of an ordinary worker in clinical chemistry.

The assay is carried out at a pH of 9 or less, and preferably from about 7 to about 9. Any suitable buffer or mixture of buffers can be used in the practice of this invention as long as it is capable of maintaining the pH during the assay at 9 or less. Particularly useful buffers are nitrogen-containing organic buffers, many of which are standard in the art [for example, see Good et al, *Biochem*, 5(2), 1966, pp. 467–477]. Representative buffers include, but are not limited to, the group consisting of tris(hydroxymethyl)aminoethane.HCl, glycylglycine, N-tris(hydroxymethyl)-methyl-2-aminoethanesulfonic acid and N-2-hydroxyethylpiperazine-N'-2-ethanesulfonic acid. The first buffer is most preferred.

The buffer can be located in any zone of the element. However, in a preferred embodiment described and claimed in copending and commonly assigned U.S. Ser. No. 900,069, filed on even date herewith and noted above, substantially all of the buffer is located in the spreading zone (described below) of the element of this invention. This means that substantially little buffer is located in other zones of the element. More particularly, at least about 80% of the buffer is located in the spreading zone. The buffer is present therein in a suitable amount, depending upon the particular buffer, to maintain the pH of the reaction mixture at the desired pH of 9 or less. These buffering amounts can easily be determined by one of ordinary skill in clinical chemistry, but is generally at least about about 1 g/m².

Other optional reagents can also be added to the element, if desired. For example, metal ion activators can be added to activate the isoenzymes. Such activators include divalent cations such as $Mg^{++}$, $Co^{++}$, $Mn^{++}$, $Ca^{++}$, $Zn^{++}$, $Sr^{++}$ and $Fe^{++}$, available in free or salt form (for example, aspartate, acetate, chloride or sulfate). Alternatively, if the levels of endogenous alkaline phsophatase in the test sample are abnormally high, inhibitors of the enzyme activity may be used. Useful inhibitors include phenylalanine and tetramisole. Such inhibitors advantageously do not affect the activity of some nonhuman alkaline phosphatase isoenzymes.

In addition, one or more phosphate acceptors are preferably included in the element to increase the rate of enzyme reaction when phosphate substrates are used. Useful phosphate acceptors include aminoalcohols or derivatives thereof, or aliphatic amines with the amino alcohols being particularly useful. Examples of such compounds are well known in the art.

Glycerol or another humectant can be added to one or more zones of the element in order to reduce element curl.

The method of this invention is practiced with a dry analytical element which comprises an absorbent carrier material, for example a thin sheet of a self-supporting absorbent or bibulous material, such as filter paper or strips, which contains the buffer, isoenzyme and substrate described above. The element is divided into at least two zones and the isoenzyme and substrate are incorporated into individual zones. Such elements are known in the art as test strips, diagnostic elements, dip sticks or diagnostic agents.

The reagents can be incorporated into a suitable absorbent carrier material by inhibition, impregnation, coating or other suitable technique. Useful absorbent materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and other suitable materials. Useful materials and procedures for making such elements are well known in the art.

The two zones can be separate layers, or finite areas within a single layer. They can be composed of the same or different materials and joined by lamination or other standard techniques. Preferably, as described in our U.S. Ser. No. 900,069, noted above, at least one of the two zones is a porous spreading zone (described below).

The two zones of the element can be self-supporting, that is composed of materials strong enough to maintain its integrity. Preferably, the zones are carried on a support. Such a support can be any suitable dimensionally stable, and preferably, transparent (that is, radiation transmissive) material which transmits electromagnetic radiation of a wavelength between about 200 and about 900 nm. A support of choice for a particular element should be compatible with the intended mode of detection (reflection or transmission spectroscopy). Useful support materials include paper, metal foils, polystyrene, polyester, polycarbonates, cellulose esters and others known in the art.

The porous spreading zone can be prepared from any suitable fibrous or non-fibrous material or mixtures of either or both. The void volume and average pore size of this zone can be varied depending upon the use intended. For example, if whole blood or other liquid samples containing high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (for example, blush polymers) or particulate materials, as described in U.S. Pat. Nos. 3,992,158 (issued Nov. 16, 1976 to Przybylowicz et al), 4,258,001 (issued Mar. 24, 1981 to Pierce et al), and U.S. Pat. No. 4,430,436 (issued Feb. 7, 1984 to Koyama et al) and Japanese Patent Publication No. 57(1982)-101760 (published June 24, 1982). It is desirable that the spreading zone be isotropically porous, meaning that the porosity is the same in each direction in the zone as caused by interconnected spaces or pores between particles, fibers or polymeric strands.

Most preferably, the porous spreading zone is prepared as a blush polymer layer as described in U.S. Pat. No. 3,992,158, noted above.

The elements have two essential zones, at least one of which can be a porous spreading zone. The other essential zone can be a reagent zone or a registration zone as those zones are known in the art. The element can have other zones including, but not limited to, additional spreading zones, radiation-blocking or radiation-filtering zones, subbing zones or barrier zones. Preferably, there is a subbing zone located between the two essential zones. The subbing zone provides adhesion between zones and helps to insure that the isoenzyme and substrate do not interact prior to the assay. All zones in the element are generally in fluid contact with each other, meaning that fluids, reagents and reaction products (for example, color dyes) can pass or be transported between superposed regions of adjacent zones. Preferably, the zones are separately coated layers, although two or more zones can be a single layer. Besides the references noted above, suitable element components are described, for example, in U.S. Pat. Nos. 4,042,335 (issued Aug. 16, 1977 to Clément), 4,132,528 (issued Jan. 2, 1979 to Eikenberry et al) and 4,144,306 (issued Mar. 13, 1979 to Figueras).

A preferred embodiment of this invention is an element comprising a support having thereon, in order and in fluid contact, a layer containing the isoenzyme described herein, a radiation-blocking layer, a subbing layer, and a porous spreading layer which contains a substrate for the isoenzyme and the buffer as described above. The isoenzyme layer can be a porous spreading layer also, but preferably, it is a reagent or registration layer containing one or more hydrophilic binders (for example, gelatin, vinyl pyrrolidone polymers or acrylamide polymers) surfactants, mordants, and other addenda. The subbing layer can comprise one or more subbing materials known to one skilled in the art, for example, vinyl pyrrolidone polymers or acrylamide polymers. The radiation-blocking layer generally includes one or more binders, surfactants and reflective materials which are known in the art.

Optionally, this preferred element can also include a second porous spreading layer which is the outermost layer of the element, and which is generally contiguous to the first porous spreading layer. The second porous spreading layer can be constructed of materials the same as or different than those of the first porous spreading layer containing the isoenzyme substrate. For example, the first spreading layer containing the buffer can comprise blush polymers according to U.S. Pat. No. 3,992,158, noted above, and the second spreading layer can be composed of particulate materials as described above. This second spreading layer can also contain buffer if desired.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, theophylline determination is made by taking the element from a supply roll, chip packet or other source and physically contacting it with a sample (for example, less than 200 $\mu$l) of the liquid to be tested. Such contact can be accomplished in any suitable manner, for example, by dipping or immersing the element into the sample or, preferably, by spotting the element by hand or machine with a drop of the sample with a suitable dispensing means.

After sample application, the element is exposed to any conditioning, such as incubation or heating, that may be desirable to quicken or otherwise facilitate obtaining any test result.

The alkaline phosphatase present in the element then catalyzes reaction of the substrate at a rate based on the amount of alkaline phosphatase present which is not inhibited by theophylline in the sample. The rate of detectable change (for example, dye formation) due to formation of the reaction product is quantifiable using suitable apparatus for reflection or transmission spectrophotometry. Suitable spectrophotometric apparatus and procedures are known in the art. Other suitable detection means include the use of fluorescence spectrophotometry, radiometry or enzyme labeling. The amount of theophylline is inversely proportional to the measured reaction rate.

For example, when p-nitrophenyl phosphate is used as the substrate, the uninhibited enzymatic reaction produces p-nitrophenol which is measurable at 400 nm using a standard spectrophotometer. The rate of the quantifiable color change can then be directly related to the rate of substrate reaction which, in turn, is indirectly related to the concentration of theophylline in the sample.

In the following examples, which are provided to illustrate the practice of the invention, the materials used were obtained as follows:

Beef liver alkaline phosphatase isoenzyme, p-nitrophenyl phosphate and tris(hydroxymethyl)aminomethane.HCl buffer from Sigma Chemical Co. (St. Louis, Mo.), polyurethane resin as ESTANE from B. F. Goodrich (Cleveland, Ohio), BRIJ 78 surfactant from Ruger (Irvington, N.J.), DAXAD 30S surfactant from W. R. Grace (Lexington, Mass.), lyophilized albumin from Miles Laboratories, (Elkhart, Ind.), TRITON X-100, X-200E and X-405 surfactants from Rohm & Haas (Philadelphia, Pa.), and the remaining materials from Eastman Organic Chemicals (Rochester, N.Y.), or prepared using standard starting materials and procedures.

EXAMPLES 1–2

Comparative Examples of Elements

These examples are comparisons of an assay and element of the present invention to assays and elements similar to that described in copending and commonly assigned in U.S. Ser. No. 692,473, noted above. It can be seen from the data presented below that the assay of this invention exhibits reduced interference from endogenous alkaline phosphatase and hemoglobin over the Control assays.

The element of this invention was prepared having the following format and components:

| | | Range |
|---|---|---|
| Spreading Layer | Titanium dioxide | 20–50 g/m$^2$ |
| | Cellulose acetate | 5–15 g/m$^2$ |
| | Polyurethane resin (ESTANE) | 0.5–5 g/m$^2$ |
| | TRITON X-405 surfactant | 0.1–10 g/m$^2$ |
| | p-Nitrophenyl phosphate | 1–5 g/m$^2$ |
| | BRIJ 78 surfactant | 0.1–3 g/m$^2$ |
| | Tris(hydroxymethyl)-aminomethane.HCl buffer (pH 8) | 1–10 g/m$^2$ |
| Subbing Layer | Poly(N—isopropyl-acrylamide | 0.1–1 g/m$^2$ |
| | TRITON X-100 surfactant | 0.01–1 g/m$^2$ |
| Radiation Blocking Layer | Gelatin (hardened) | 1–15 g/m$^2$ |
| | TRITON X-200E surfactant | 0.01–1 g/m$^2$ |
| | Titanium dioxide | 20–50 g/m$^2$ |
| | DAXAD 30S surfactant | 0.05–0.5 g/m$^2$ |
| | Tris(hydroxymethyl)-aminomethane.HCl buffer (pH 8) | 0.1–1 g/m$^2$ |
| | Glycerol | 0.1–2.5 g/m$^2$ |
| | Piperazine-N,N'—bis-(2-hydroxypropane sulfonic acid) | 0.1–1 g/m$^2$ |
| Registration Layer | Gelatin (hardened) | 2–20 g/m$^2$ |
| | Alkaline phosphatase beef liver isoenzyme | (See Table I below) |
| | Tris(hydroxymethyl)-aminomethane.HCl buffer (pH 8) | 0.1–1 g/m$^2$ |
| | Magnesium chloride | 0.005–0.1 g/m$^2$ |
| | TRITON X-100 surfactant | 0.1–2 g/m$^2$ |
| | Poly(styrene-co-N—vinyl-benzyl-N—benzyl-N,N—dimethylammonium chloride-co-divinyl-benzene) | 0.5–1.5 g/m$^2$ |
| | Glycerol | 0.1–2.5 g/m$^2$ |
| | Lyophilized albumin | 0.01–0.15 g/m$^2$ |
| | Poly(ethylene terephthalate) | |

-continued

| Support | Range |
|---|---|

Control elements were similarly prepared except that the amount of alkaline phosphatase isoenzyme in the registration layer was less than 100 I.U./m² (see Table I below).

The elements were used to determine theophylline in the following manner. Two test fluids were prepared, each containing 18.5 μg/ml of theophylline. To one of these fluids was added 1000 I.U. of human alkaline phosphatase. The theophylline concentration of each test fluid was determined by dropping a 10 μl volume sample of the fluid onto the porous spreading layer of each element. During incubation at 37° C., the rate of enzyme activity was measured by monitoring the absorbance of resulting dye at 410 nm using a standard clinical chemistry analyzer.

The results are shown in Table I below. Bias (μg/ml) was determined by comparing the predicted concentrations of paired human sera containing theophylline with and without 1000 I.U. of human alkaline phosphatase. Acceptable bias is less than 3 μg/ml. It is apparent that the Control element exhibited unacceptable bias from the endogenous alkaline phosphatase whereas the elements of the present invention exhibited significantly less bias.

TABLE I

| Element | Alkaline Phosphatase Isoenzyme Concentration (I.U./m²) | Bias |
|---|---|---|
| Control A | 61 | −5.12 |
| Control B | 93 | −3.48 |
| Example 1 | 123 | −2.62 |
| Example 2 | 184 | −2.05 |

It was also observed that this improvement in bias was achieved after the elements of this invention had been stored at 25° C. and 15% relative humidity for 1 week. The elements of this invention appear to exhibit improved keeping properties. All of the elements described above were evaluated after the keeping period by applying test fluids containing various amounts of theophylline (0.9–37.5 μg/ml) to the spreading layer and measuring the dye formed as described above. Table II below shows the results of these tests. The bias is acceptably low at all theophylline concentrations using the elements of the present invention. The Control elements did not exhibit acceptable bias (3 μg/ml or less) at all concentrations.

TABLE II

| | Bias (μg/ml) Theophylline Concentration (μg/ml) | | |
|---|---|---|---|
| Element | 0.9 | 9.5 | 37.5 |
| Control A | 0.1 | −2.34 | −6.27 |
| Control B | −0.59 | 2.32 | −3.16 |
| Example 1 | −0.66 | 0.58 | 1.79 |
| Example 2 | 0.02 | 2.57 | −0.16 |

In addition, the elements of this invention exhibited a rate range increase up to 80% over the Control elements.

EXAMPLE 3

Comparison of Elements and Assays for Hemoglobin Bias

An element of this invention like Example 2 above was compared to a element like Control A above in an assay for theophylline (20 μg/ml), and the bias due to hemoglobin (150 mg/dl) was evaluated. The elements were tested as described in Examples 1 and 2 using a test fluid containing the indicated amounts of theophylline and hemoglobin. The bias was determined by comparing the predicted concentrations of the fluid with and without hemoglobin at the same theophylline level.

Table III below shows the results of these tests. The element of this invention exhibited significantly less bias from the hemoglobin as compared to the Control element. A bias of less than about 2 μg/ml is acceptable.

TABLE III

| Element | Bias (μg/ml) |
|---|---|
| Control | −2.03 |
| Example 3 | −0.85 |

The invention has been described in detail with particular reference to preferred embodiments thereof, but it will be understood that variations and modifications can be effected within the spirit and scope of the invention.

We claim:

1. A dry analytical element for the determination of theophylline comprising an absorbent carrier material, a buffer which maintains the pH at 9 or less during the determination and, in fluid contact, first and second zones, said first zone containing at least about 100 I.U./m² of an isoenzyme of alkaline phosphatase which is capable of acting on a substrate for said isoenzyme at a pH of 9 or less, and said second zone containing a substrate for said isoenzyme.

2. The element of claim 1 wherein said isoenzyme is present in an amount of at least about 150 I.U./m².

3. The element of claim 1 where in said substrate is an organic mono- or diester of phosphoric acid.

4. The element of claim 3 wherein said substrate is selected from the group consisting of p-nitrophenyl phosphate and 4-(4-nitro-2-methylsulfonyl phenylazo)-naphthol-1-phosphate.

5. The element of claim 1 wherein said isoenzyme is bovine liver alkaline phosphatase.

6. A dry analytical element for the determination of theophylline comprising, in fluid contact, a porous spreading zone and at least one additional zone, said element containing at least about 100 I.U./m² of an isoenzyme of alkaline phosphatase which is capable of acting on a substrate for said isoenzyme at a pH of 9 or less, and a substrate for said isoenzyme, provided said phosphatase and substrate are in different zones of said element, said element further containing a buffer which is capable of maintaining the pH at 9 or less during said determination, provided that substantially all of said buffer is in said porous spreading zone.

7. The element of claim 6 wherein said isoenzyme is present in an amount of at least about 150 I.U./m².

8. The element of claim 6 wherein said phosphatase substrate is in said spreading zone.

9. An analytical element for the determination of theophylline comprising: a support having thereon, in order and in fluid contact:

a first layer containing at least about 150 I.U./m² of an isoenzyme of alkaline phosphatase which is capable of acting on a substrate for said isoenzyme at a pH of 9 or less, a radiation-blocking layer, and a porous spreading layer containing a substrate for said isoenzyme, said element further containing a buffer which is capable of maintaining the pH at 9 or less during said determination, provided that substantially all of said buffer is in said porous spreading layer.

10. The element of claim 9 further comprising a subbing layer between said radiation-blocking and porous spreading layers.

11. The element of claim 9 wherein said porous spreading layer is a blush polymer spreading layer.

12. The element of claim 11 wherein said porous spreading layer comprises titanium dioxide.

13. A method for the determination of theophylline comprising the steps of:

A. at a pH of 9 or less, contacting a sample of a biological fluid suspected of containing theophylline with a dry analytical element comprising an absorbent carrier material, a buffer which maintains the pH at 9 or less during the determination and, in fluid contact, first and second zones, said first zone containing at least about 100 I.U./m² of an isoenzyme of alkaline phosphatase which is capable of acting on a substrate for said isoenzyme at a pH of 9 or less, and said second zone containing a substrate for said isoenzyme, and B. determining a detectable change resulting from said contact.

14. The method of claim 13 carried out at a pH of from about 7 to about 9.

15. The method of claim 13 wherein said biological fluid is human blood serum or whole blood.

16. A method for the determination of theophylline comprising the steps of:

A. at a pH of 9 or less, contacting a sample of a human biological fluid suspected of containing theophylline with a dry analytical element comprising: a support having thereon, in order and in fluid contact:

a first layer containing at least about 150 I.U./m² of an isoenzyme of alkaline phosphatase which is capable of acting on a substrate for said isoenzyme at a pH of 9 or less, a radiation-blocking layer, and a porous spreading layer containing a substrate for said isoenzyme, said element further containing a buffer which is capable of maintaining the pH at 9 or less during said determination, provided that substantially all of said buffer is in said porous spreading layer, and B. determining a detectable change resulting from said contact.

17. The method of claim 16 carried out at a pH of from about 7 to about 9.

18. The method of claim 16 wherein said human biological fluid is blood serum or whole blood.

* * * * *